United States Patent [19]

Volz et al.

[11] 4,383,337
[45] May 17, 1983

[54] ELBOW PROSTHESIS

[75] Inventors: Robert G. Volz, Tucson, Ariz.; Richard R. Vanzile; Richard C. Bolesky, both of Warsaw, Ind.

[73] Assignee: Zimmer USA, Inc., Warsaw, Ind.

[21] Appl. No.: 199,491

[22] Filed: Oct. 22, 1980

[51] Int. Cl.³ .............................................. A61F 1/04
[52] U.S. Cl. ..................................... 3/1.91; 128/92 C
[58] Field of Search ............................. 3/1.91, 1.911; 128/92 C

[56] References Cited

U.S. PATENT DOCUMENTS

| | | | |
|---|---|---|---|
| 2,696,817 | 12/1954 | Prevo | 3/1 |
| 3,638,243 | 2/1972 | Campbell, Jr. et al. | 3/1 |
| 3,656,186 | 4/1972 | Dee | 3/1 |
| 3,708,805 | 1/1973 | Scale et al. | 3/1 |
| 3,728,742 | 4/1973 | Averill et al. | 3/1 |
| 3,748,662 | 7/1973 | Hefel | 3/1 |
| 3,772,709 | 11/1973 | Swanson | 3/1 |
| 3,774,244 | 11/1973 | Walker | 3/1 |
| 3,813,700 | 6/1974 | Tavernetti et al. | 3/1 |
| 3,816,854 | 6/1974 | Schlein | 3/1.91 |
| 3,837,009 | 9/1974 | Walker | 3/1 |
| 3,868,730 | 3/1975 | Kaufer et al. | 3/1 |
| 3,879,766 | 4/1975 | Lowe et al. | 3/1.91 |
| 3,919,725 | 11/1975 | Swanson et al. | 3/1.91 |
| 3,939,496 | 2/1976 | Ling et al. | 3/1.91 |
| 3,990,117 | 11/1976 | Pritchard et al. | 3/1.91 |
| 3,990,118 | 11/1976 | Strickland et al. | 3/1.91 |
| 4,038,704 | 8/1977 | Ring | 3/1.91 |
| 4,055,862 | 11/1977 | Farling | 3/1.91 |
| 4,057,858 | 11/1977 | Helfet | 3/1.91 |
| 4,079,469 | 3/1978 | Wadsworth | 3/1.91 |
| 4,106,128 | 8/1978 | Greenwald et al. | 3/1.91 |
| 4,112,522 | 9/1978 | Dadurian et al. | 3/1.91 |
| 4,156,296 | 5/1979 | Johnson et al. | 3/1.91 |
| 4,194,250 | 3/1980 | Walker | 3/1.91 |
| 4,224,695 | 9/1980 | Grundei et al. | 3/1.91 |
| 4,274,163 | 6/1981 | Malcom et al. | 3/1.91 |
| 4,293,963 | 10/1981 | Gold | 3/1.91 |

FOREIGN PATENT DOCUMENTS

| | | | |
|---|---|---|---|
| 1520162 | 8/1978 | United Kingdom | 3/1.91 |
| 1528906 | 10/1978 | United Kingdom | 3/1.91 |
| 1537479 | 12/1978 | United Kingdom | 3/1.91 |

Primary Examiner—Richard J. Apley
Assistant Examiner—David J. Isabella
Attorney, Agent, or Firm—Sherman & Shalloway

[57] ABSTRACT

A humeral member and an ulnar member are joined by an intermediate insert which functions as an ulnar bushing. A radial member may also be employed with the prosthesis. The ulnar member includes a curved surface from which a support projects. Preferably, the curved surface is in concave cylindrical form from which a flat support radially projects. The support terminates in a cylindrical member which has an axis located at the center of the curvature of the curved surface. The ulnar bushing is of generally cylindrical configuration and is mounted about the cylindrical member for rotation. The humeral member engages the intermediate insert allowing relative rotation between the ulnar member and the intermediate insert along with the humeral member. A spherical portion projects from the side of the humeral member and has an axis parallel to the axis of rotation of the ulnar member. The spherical portion is for contact with the radius or radial member. The radial member has a concave spherical surface for engaging the spherical portion and may include a circular X-ray wire in a top portion thereof.

11 Claims, 21 Drawing Figures

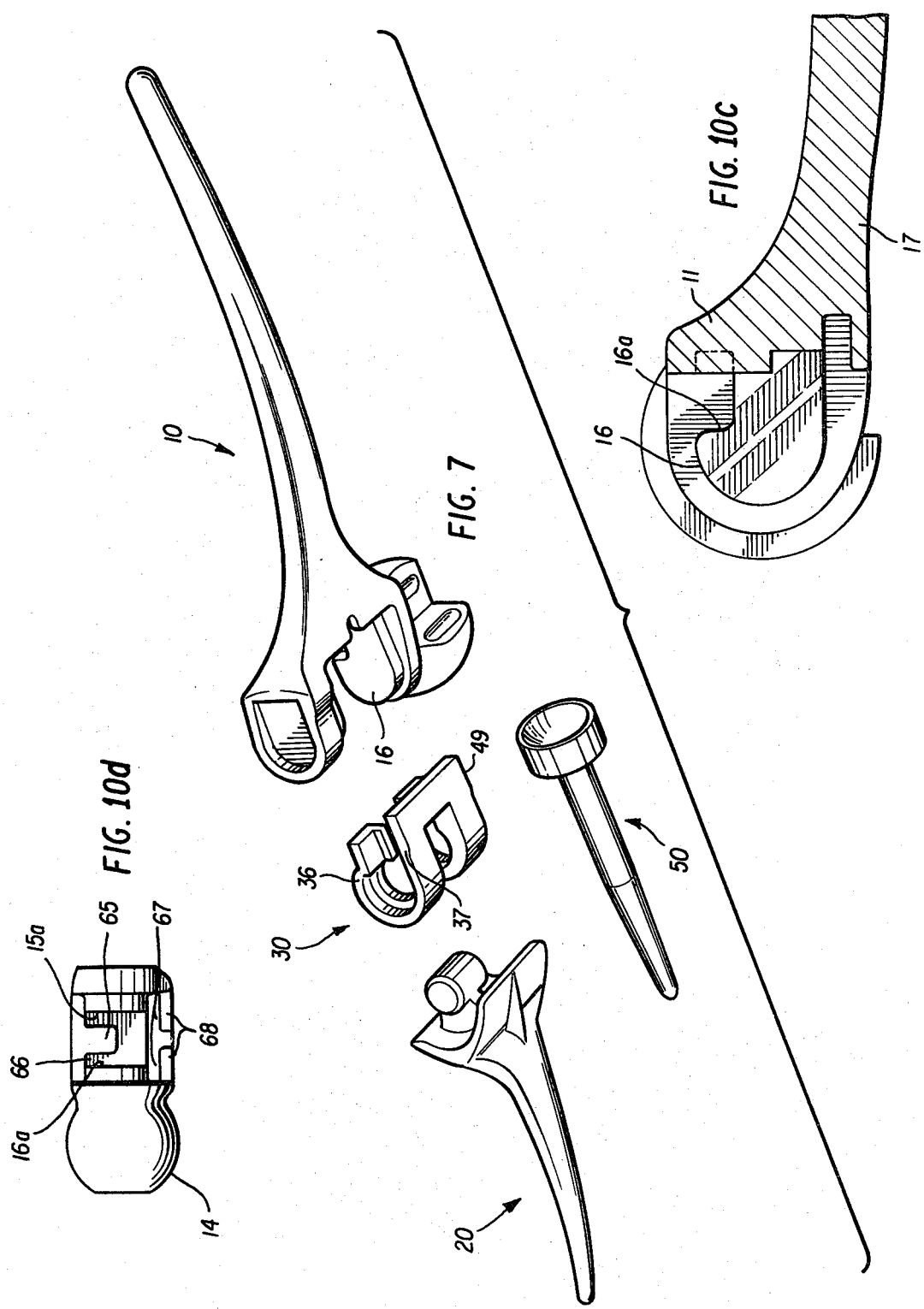

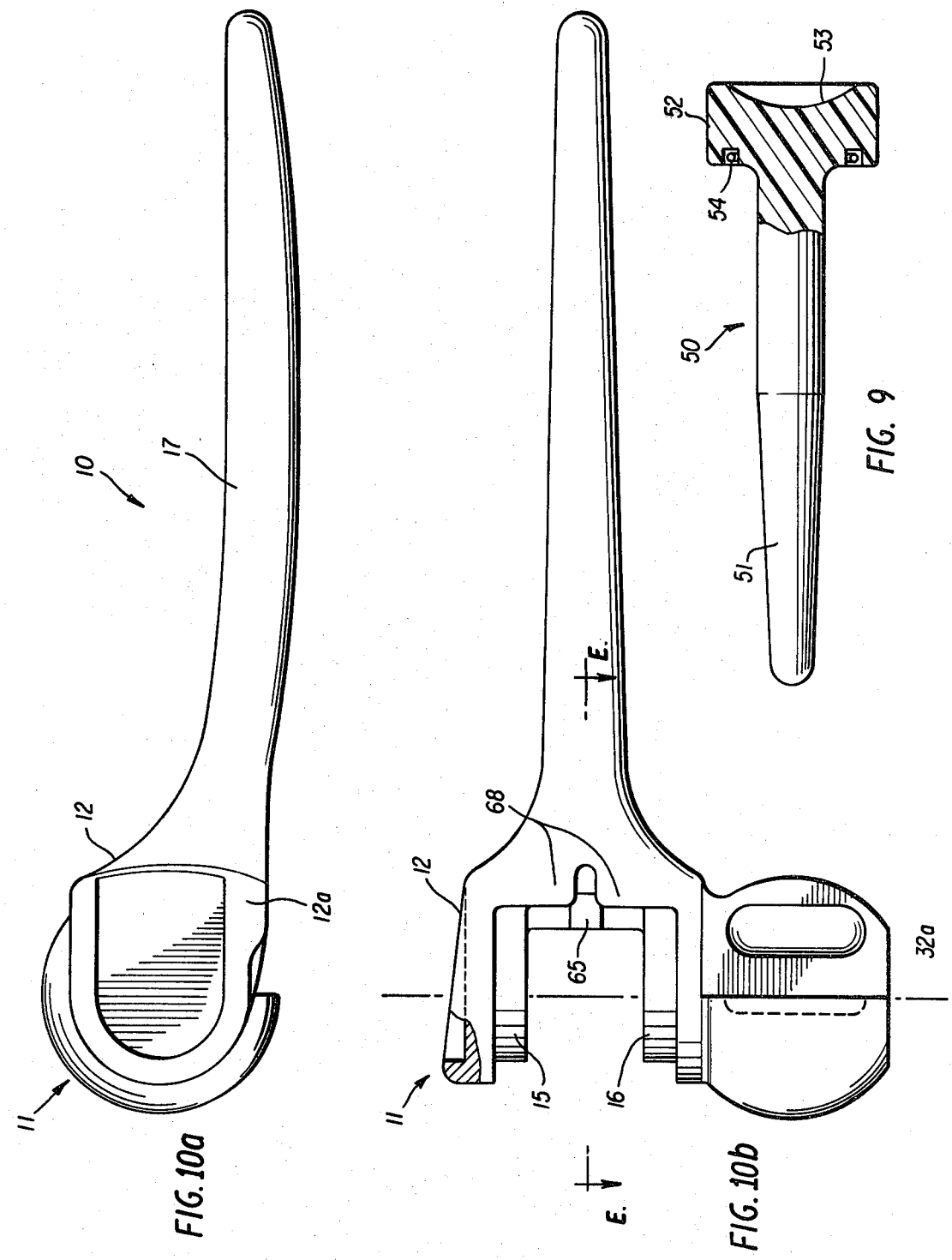

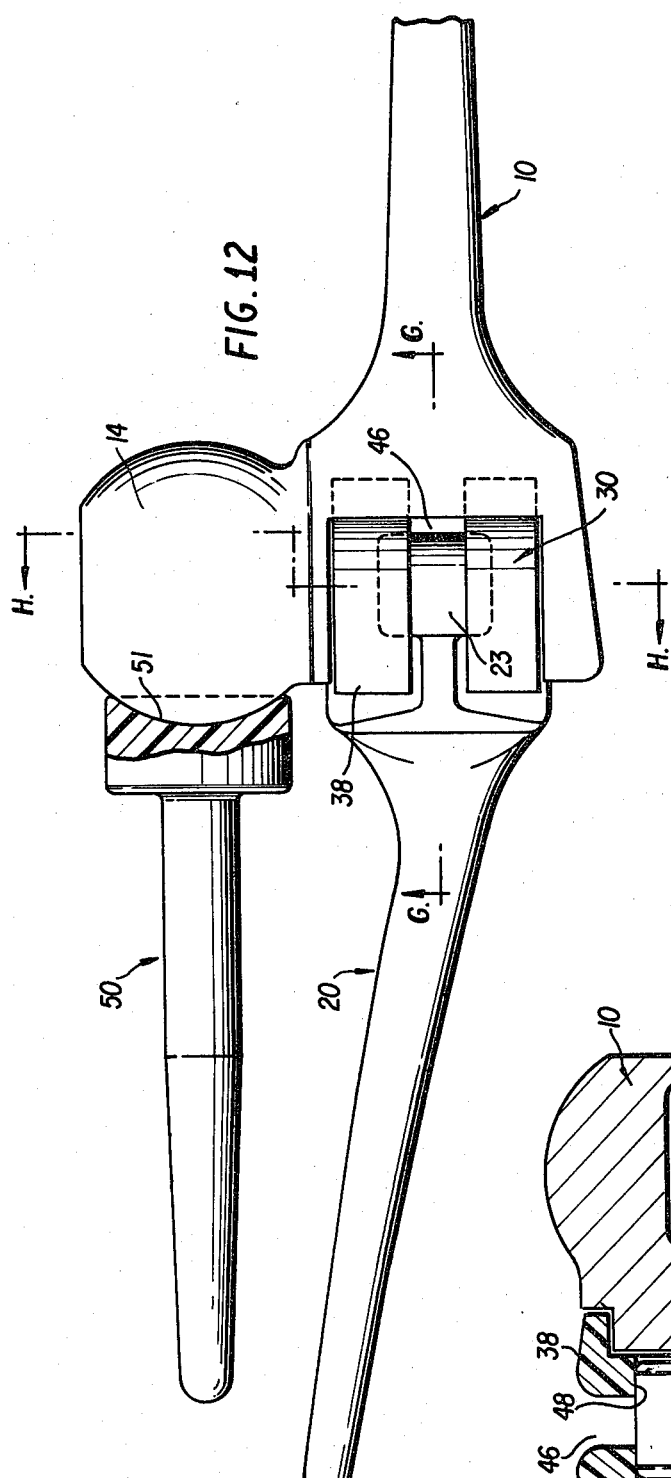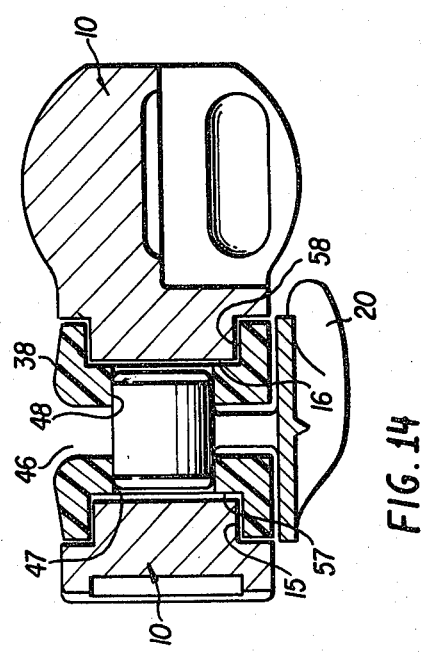

ELBOW PROSTHESIS

BACKGROUND OF THE INVENTION

1. Field of the Invention

The invention generally relates to bone joint prosthesis and, more particularly, is concerned with an elbow prosthesis which allows for the three planes of motion normally occurring in the humeral-ulnar joint.

2. DESCRIPTION OF THE PRIOR ART

U.S. Pat. No. 3,816,854 to Schlein discloses a prosthesis for the elbow joint including a humeral component terminating in a partial cylinder and is provided with a slot. The ulnar component includes a U-shaped member having arms for supporting a pin. The pin engages the slot in the bearing member to provide rotation between the components.

Other types of prior art, as exemplified by U.S. Pat. No. 3,919,725, issued to Swanson, et al., describe an elbow joint prosthesis which uses a cap intermediate the humeral and ulnar portions.

U.S. Pat. No. 4,079,469, issued to Wadsworth, discloses a semi-globular portion for engaging the radius of an elbow prosthesis.

U.S. Pat. No 3,868,730 to Kaufer, et al. and U.S. Pat. No. 4,112,522 to Dadurian, et al., disclose other examples of joint prosthesis which employ inserts between rotating members.

SUMMARY OF THE INVENTION

It is an object of this invention to describe a total elbow prosthesis having a semi-constrained interface which allows for the three planes of motion normally occurring at the humeralulnar joint.

It is another object of this invention to describe a total elbow prosthesis allowing for radial-capitellar surface replacement resulting in a significant decrease in stresses placed upon the bone-cement-medullary system composite.

It is another object of this invention to describe a total elbow prosthesis having a resistance to subluxation and dislocation with distractive forces up to 50 kilograms.

It is yet another object of this invention to describe a total elbow prosthesis having anatomically shaped intramedullary systems which lessen the need for cortical bone removal.

It is still another object of this invention to describe a total elbow joint prosthesis which requires minimal bone resection for insertion permitting the preservation of medial and lateral condyles and the olecranon.

The elbow is a joint of complex planes of motion. It has been observed that the ulna flexes and extends upon the humerus and changes of up to 20° and the arc of rotation of varus-valgus alignment occure. The soft tissue supporting the elbow, as at the knee, play an important role in the stability and its ability to dissipate significant joint stresses. Thus, when the elbow is subjected to forceful extension, such as may occur with throwing a baseball, terminal extension is dampened by the shock absorbing action of the trochlear fat pad located between the trochlear notch and the tip of the olecranon. Resistance to hyperextension is also offered by the interior joint capsule which becomes taut with full extension. Medial-lateral stability is derived from the radial and ulnar collateral ligaments, but because valgus stresses prevail at the elbow, the ulnar collateral ligament system is, by necessity, much larger and more efficient. Sacrifice of the ulnar collateral ligament allows the elbow to angulate 15° to 20° into valgus.

It is also important to note the significant role of the radial head as a buttress against the capitellum thereby assisting in the absorption of joint stresses and preventing valgus deformity. Removal of the radial head biomechanically results in the doubling of the stresses placed upon the humeral ulnar articulation. Since the lever effect of the forearm magnifies, by factors of seven to tenfold, any weight hand-held against gravity, significant joint reactive forces above 25 kilograms can easily be reached with many activities of daily living.

The total elbow prosthesis, according to the invention, allows for the dissipation of joint stresses to the adjacent soft tissue ligaments and capsule by an interface which permits motion in three planes of freedom. The option of radial-capitellar joint replacement of the invention provides for the dissipation of joint stresses that would otherwise be borne upon the cemented intermedullary humeral and ulnar stems. Additionally, the structure of the total elbow prosthesis, according to the invention, requires only a minimal amount of bone resection for insertion. This is extremely important when considering the fact that salvage procedures following surgical removal of failed total elbows are few and generally unsatisfactory. The total elbow prosthesis of the invention allows for the preservation of the important medial and lateral condyles and their ligamentous support, in addition to the retention of nearly all the olecranon, thus, insuring the integrity of the triceps attachment.

The humeral member of the total elbow prosthesis, according to the invention, includes a fork-shaped portion terminating in a stem for engaging the medullary canal the humerus. Each branch of the fork of the humeral member is flat and the branches are formed in parallel planes. The outer surface of one fork branch has a ridge thereon and the outer surface of the other fork branch carries a spherical member projecting from the side of the fork and having an axis parallel to the axis of rotation. The spherical portion contacts the radius or radial member. The inside surface of each fork branch includes a platform having a notch therein. The notches are opposite each other so that each platform is a mirror image of the other and the platform is in the form of an inverted L with a rounded top.

The opposing ulnar member includes a shaft for engaging the medullary canal the ulna and terminating in a curved surface in the form of a partial cylinder. A support projects from the curved surface in a plane parallel with the stem and perpendicular to the curved surface. The support terminates in a cylindrical member which has an axis located at the center of curvature of the curved surface. This axis is coaxial with the axis of rotation of the total elbow prosthesis.

The intermediate insert used to join the humeral member and the ulnar member is comprised of an integral plastic unit including a means for engaging the cylindrical member of the ulnar member and a means for engaging the platforms of the humeral member. The insert is generally U-shaped and has an axis located at the center of the curvature of the base of the U-shape coaxial with the axis of rotation of the total elbow prosthesis. A slot is formed in one leg of the U-shape perpendicular to the axis of the center of the curvature of the lower portion of the U-shape. This slow allows the cylindical member which projects from the curved surface of the radial member to be inserted between the legs of the U-shape so that the axis of the cylindrical member corresponds to the axis of the base of the U-shape. The outer portions of the insert are slotted for receiving the platforms of the humeral member. Each slot includes a notch which engages the notch of the humeral member thereby interconnecting the ulnar member and the humeral member.

An optional radial member is also contemplated. The radial member is comprised of an integral plastic portion having a stem terminating in a disc perpendicularly attached to the stem. The face of the disc has a slightly concave surface for engaging the spherical portion projecting from the side of the humeral member.

BRIEF DESCRIPTION OF THE DRAWINGS

These features and objects of the invention, as well as others, will become apparent to those skilled in the art by referring to the accompanying drawings in which:

FIG. 7 is a prospective view of the total elbow prosthesis according to the invention;

FIG. 8c is a sectional view of the intermediate insert taken along lines C—C of FIG. 8a;

FIG. 9 is a partial longitudinal view with parts broken away of the radial member according to the invention;

FIGS. 10a and 10b are side and bottom views of the right humeral member of the elbow prosthesis according to the invention;

FIG. 10c is a sectional view taken along lines E—E of FIG. 10b;

FIG. 10d is an end view of the right humeral member of the elbow prosthesis according to the invention;

FIG. 12 is a view of the assembled right elbow prosthesis according to the invention;

FIG. 14 is a sectional view of the assembled right elbow prosthesis taken along lines H—H of FIG. 12.

SURGICAL PROCEDURE FOR IMPLANTING THE PROSTHESIS

The patient is supinely positioned upon the operating table and the involved elbow is acutely flexed across the chest. Pneumatic tourniquet hemostasis is routinely advised.

Figure 1:
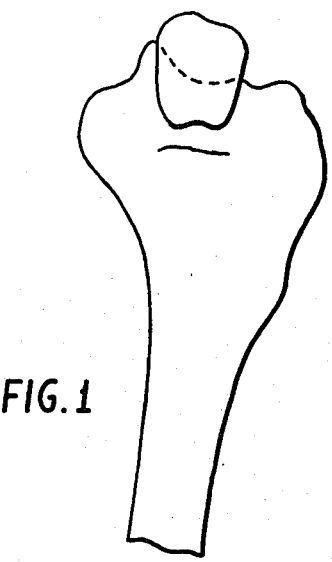
FIGS. 1-6 illustrate the steps of the surgical procedure employed to implant the total elbow prosthesis according to the invention.

A vertical posterior curvilinear incision is placed slightly radialward. Bleeding points are controlled by electrocautery. Identification and retraction of the ulnar nerve is optional. In the absence of deformity to the olecranon, (the triceps olecranon), the triceps is either detached subperiosteally or sectioned more proximally at its musculo tendinous junction. The posterior capsule is incised and the tip of the olecranon removed (FIG. 1) by use of a reciprocating saw to improve visualization of the trochlear notch.

Dissection is carried laterally where reflection of the capsular-ligamentous-tendinous complex from the condyle is completed, thereby facilitating exposure of anterior surface of the capitellum and the radial head.

Figure 2:
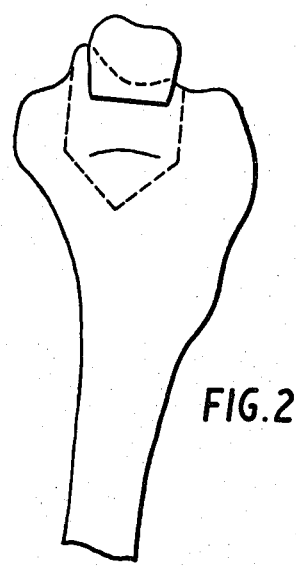
Figure 3:
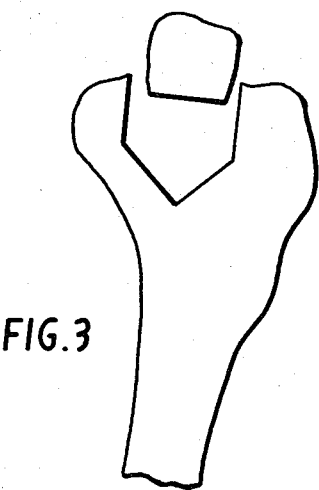
Figure 4:
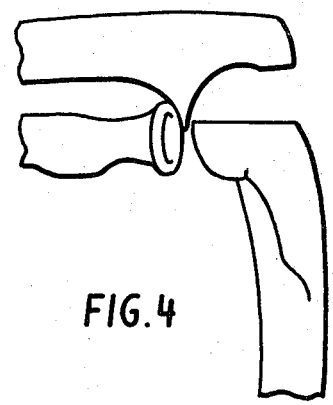
Figure 5:
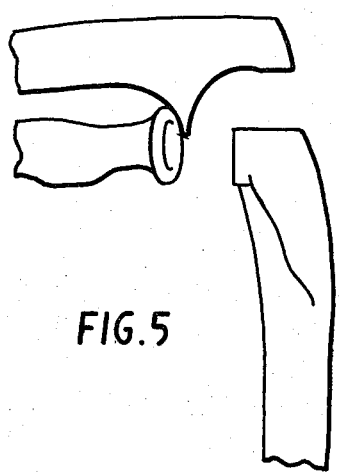

Next, by use of a reciprocating saw, the bone of the trochlear notch is excised (FIG. 2) with care being taken to preserve the important medial and lateral condylar bone masses. Approximately ⅜ in. of the capitellum is then removed in a horizontal plane (FIG. 3), followed by the removal of the anterior surface of the capitellum in a plane parallel with the anterior humeral cortex (FIG. 4). The radial head is now identified and excised through its neck (FIG. 5).

Figure 6:
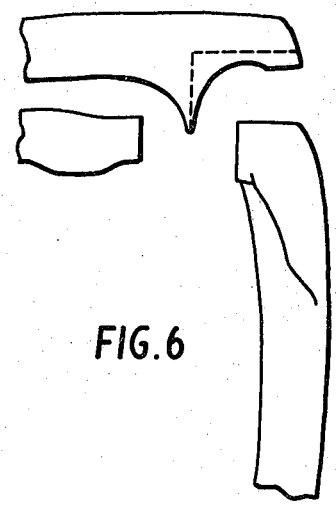

Lastly, the articular plate of the olecranon is removed first with a horizontal and then a vertical cut each at ninety degrees one to the other (FIG. 6). Care should be taken to preserve as much olecranon bone as possible so as to provide an adequate bone mass for the insertion of the triceps.

In cases of severe dishing of the olecranon, as seen in rheumatoid patients, the olecranon can be shortened by the segmental resection of bone; reattachment of olecranon tip with its intact triceps tendon is later achieved by wire fixation.

By use of drills, curettes, and broaches the humeral, ulnar and radial canals are reamed until all cancellous bone has been removed and prosthetic stem insertion can be performed easily. A trial fit of all prosthetic components without the intermediate insert is carried out. If full extension cannot be easily achieved, it may be necessary to remove the anterior capsule or shorten the humerus.

Throughout the procedure, the operative site and adjacent exposed tissues should be kept moist with a topical antibiotic irrigant. Prior to cementing of component parts, all bony beds should be copiously irrigated to remove blood, fat and bone debris and then dried. Plugging of the humeral canal followed by cement injection by syringe technique is highly recommended.

Usually, the ulnar and radial components are cemented together prior to the humeral component. The radial head must be precisely positioned in relationship to the ulnar component, as this relationship will affect the eventual articulation of the humeral component to each of these components. The articulating surface of the radial head must be exactly located at a level flush with the concave articulating surface of the ulnar component.

All excess cement should be removed following insertion of components. The intermediate insert is now pressed over the olecranon trundle. The insert, after mounting on the ulnar member, is seated on the humeral member as described in the sequel.

The elbow is now placed through an arc of motion to assess alignment and stability. A layered surgical closure follows over a single suction type of drainage system. Dressings and a posterior splint are applied and maintained for five to ten days depending upon the progression of wound healing.

Wound suction drainage is discontinued twenty-four to thirty-six hours postoperatively. Depending upon the status of wound healing, active motion is permitted on the fifth to tenth postoperative day. Nighttime splinting is advised until triceps control and healing is complete. A sling should be worn during the daytime during the first twenty-one days postoperatively.

DETAILED DESCRIPTION OF THE INVENTION

Referring to FIG. 7, the basic portions of the elbow prosthesis 7, according to the invention, are the humeral member 10, the ulnar member 20, the intermediate insert 30 connecting the humeral member 10 and the ulnar member 20 and a radial member 50 engaging a portion of the humeral member 10.

The intermediate insert 30, shown in detail in FIGS. 8a–8d, has an inner bore 32 with an axis 32a which forms the pivot point of the prosthesis. The intermediate insert 30 is comprised of a first outer surface 33 and a second outer surface 34. The first outer surface is formed by a first U-shaped member 35 having a first right leg 36 and a first left leg 37. The second outer surface 34 is defined by a second U-shaped member 38 having a second right leg 39 and a second left leg 40. The first right leg 36 and the first left leg 37 are interconnected by a first bottom portion 41 and the second right leg 39 and the second left leg 40 are interconnected by a second bottom portion 42. The first U-shaped member 35 has a first slot 43 therein and the second U-shaped member 38 has a second slot 44 therein. The first left leg 37 and the second left leg 40 are interconnected by an integral platform portion 45 thereby forming an opening 46 between the first U-shaped member 35 and the second U-shaped member 38 which are interconnected by integral portion 49.

The first outer surface 33 has a first L-shaped groove 57 therein and the second outer surface 34 has a second L-shaped groove 58 therein. The inner surface of the first U-shaped member 35 defining the slot 43 has a first radial groove 47 therein. The inner surface of the second U-shaped member 38 defining the slot 44 has a second radial groove 48 therein. The first right leg 36 and second right leg 39 are notched as shown at 61 and 62, respectively, and provided with respective L-shaped protrusions 63 and 64. Preferably, the descending portions of protrusions 63 and 64, together with platform 45, form closures for radial grooves 47 and 48 of slots 43 and 44, which aid in retaining cylindrical member 23 of the ulnar member within inner bore 32 of the intermediate insert 30.

The radial component 50, shown in detail at FIG. 9, is comprised of a stem 51 terminating in a perpendicular disc-shaped portion 52. The engaging surface of the radial member 50 is a concave surface 53 and the disc-shaped portion 52 is provided with an X-ray wire 54.

The humeral member 10, shown in detail at FIGS. 10a–10d, is comprised of a stem 17 generally terminating in a fork-shaped portion 11. The fork-shaped portion 11 consists of a first flat fork branch 12 and a second flat fork branch 13. The branches 12 and 13 are in parallel planes which are perpendicular to the pivot axis 32a of the prosthesis 7. The outer surface of the second flat fork branch 13 defines a means for engaging the radial member 50 in the form of a spherical portion 14. The inner surface of the first flat fork branch 12 has integrally attached thereto, a first shoulder formed of a generally semicircular L-shaped platform 15 notched at 15A and the second flat fork branch 13 has integrally attached to its inner surface, a second shoulder formed of a generally semicircular L-shaped platform 16 notched at 16A. Ridge 12a is provided on the outer surface of branch 12. An elevated platform 65, located intermediate fork branches 12 and 13, is provided to complete the closure of bore 32 together with protrusions 63 and 64 of intermediate insert 30. Platform 65 is formed as an extension of a shoulder 66, located between the two fork branches 12 and 13.

Figure 11A:
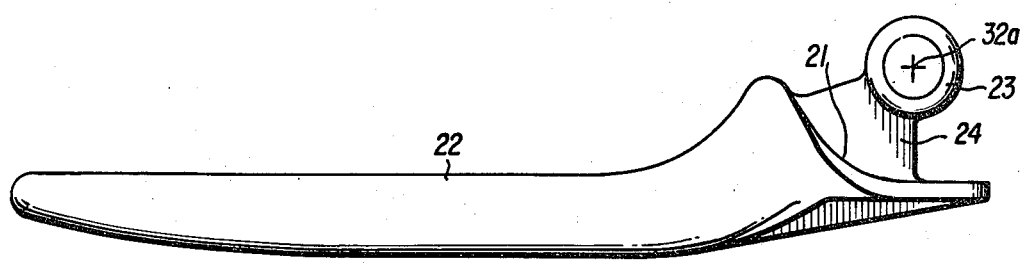
FIG. 11a is a side view of the right ulnar member of the total elbow prosthesis according to the invention.
Figure 11B:
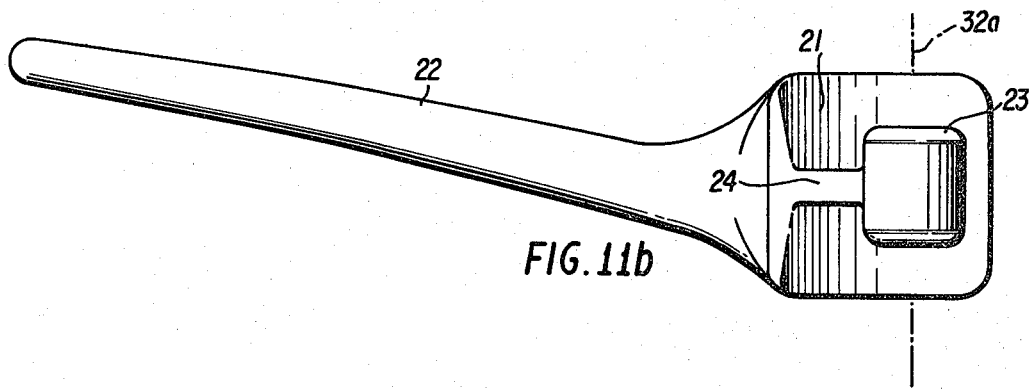
FIG. 11b is a top view of the right ulnar member of the total elbow prosthesis according to the invention.
Figure 8A:
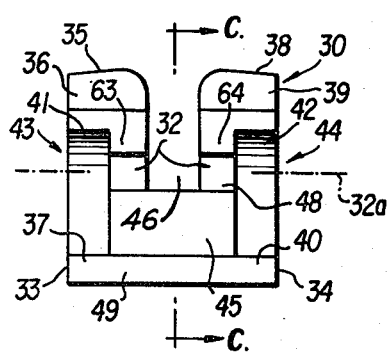
FIG. 8a is an end view taken from the humeral side of the intermediate insert.
Figure 8B:
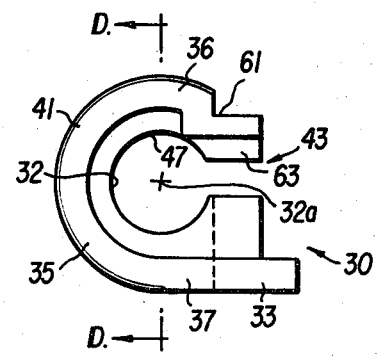
FIG. 8b is a side view of the intermediate insert of the total elbow prosthesis according to the invention.
Figure 8C:
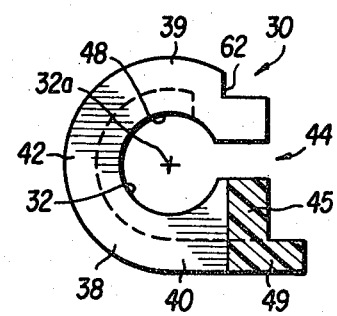
Figure 8D:
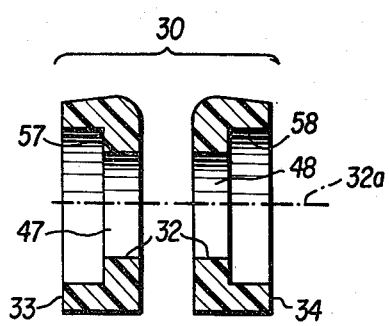
FIG. 8d is a sectional view taken along lines D—D of FIG. 8b.

The ulnar member, shown in detail in FIGS. 11a and 11b, is in the form of a stem 22 terminating in a curved surface 21. The radial point of the radius of curvature of the curved surface 21 is located at the pivot axis 32a of the prosthesis 7. The curved surface 21 is integrally attached to a support 24 which terminates in a cylindrical member 23.

Figure 13:
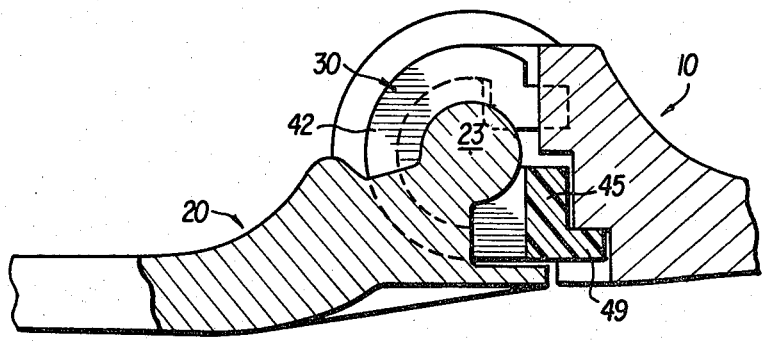
FIG. 13 is a sectional view of the assembled right elbow prosthesis taken along lines G—G of FIG. 12.

Referring generally to FIGS. 12, 13 and 14, the prosthesis is assembled in the following manner. The intermediate insert 30 is rotated 180° in a counter-clockwise direction and the cylindrical member 23 of the ulnar member 20 is inserted in the opening 46 of the intermediate insert until member 23 engages the first and second radial grooves 47 and 48. Such insertion is enabled by the flexible nature of the material of which intermediate insert 30 is formed, permitting U-shaped members 35 and 38 to spread apart in order to accept cylindrical member 23 therebetween. At this point, curved surface 21 typically contacts the outer portions of first and second bottom portions 41 and 42. The intermediate insert 30 is then rotated 180° in a clockwise direction, further separating U-shaped members 35 and 38 as the pivot axes of bore 32 and of cylindrical member 23 aligned. Once these axes are aligned, bottom portions 41 and 42 of U-shaped members 35 and 38 snap back, and with protrusions 63 and 64 substantially enclose cylindrical member 23 within grooves 47 and 48. In this condition, the curved surface 21 slides along the outer portions of first and second bottom portions 41 and 42, thus permitting rotation of the ulnar member about pivot axis 32a. The ulnar member 20 is now in locking engagement with the intermediate insert 30 which is assembled to the ulnar member 20.

In order to engage the intermediate insert 30, which is assembled to the ulnar member 20 with the humeral member 10, the insert 30 and the ulnar member 20 are moved together into engagement such that the first L-shaped groove 57 engages the first L-shaped platform 15 and the second L-shaped groove 58 engages the second platform 16. Initially, notches 61 and 62 engage shoulder 66, and L-shaped protrusions 63 and 64 engage notches 15A and 16A. Concave curved surface 21 of ulnar member 20 is then used to exert pressure against the bottom portions of first and second U-shaped members 35 and 38, causing the U-shaped membes of insert 30 to snap into more complete engagement between the descending portions of protrusions 63 and 64 and platform 65. Additional engagement is provided between L-shaped grooves 57 and 58 and the shoulders of platforms 15 and 16. Moreover, the broad surfaces of platforms 15 and 16 engage the radial portions of L-shaped grooves 57 and 58. Full rotational extension of the prosthesis, by rotation of ulnar member 20 about pivot axis 32a, exerts pressure on first and second left legs 37 and 40, causing integral interconnecting portion 49 to snap into a cavity 67, formed between a notched enclosing wall 68 and platforms 15 and 16. At this point, elevated platform 65 extends between the descending portions of L-shaped protrusions 63 and 64 to provide stabilizing positioning means therefor. As previously disclosed, platform 65 further completes the closure of bore 32, along with protrusions 63 and 64. Platform 65 may extend beyond protrusions 63 and 64, and thus, may project towards platform 45, substantially closing slots 43 and 44. The concave surface 51 of the radial member 50 is then brought into contact with the spherical portion 14.

In the preferred embodiment, the humeral member 10 and the ulnar member 20 are made of an alloy containing chrome, cobalt, and molybdenum, marketed under the trademark ZIMALOY. The radial member 30 and the intermediate member 50 are made of a biologically compatible plastic, such as ultra high molecular weight polyethylene.

To disengage an assembly prosthesis, the elbow is maximally flexed and compressive force applied thereto. The humeral member then separates from the ulnar member and intermediate insert.

Instead of the X-ray wire 54, the plastic parts may have a radioopaque substance added thereto. This substance, like the X-ray wire 54, provides a contrast medium for the purpose of locating the plastic parts on an X-ray photograph. Barium sulfate is a preferred radioopaque substance, with a preferred concentration of 7.5% by weight, although permissible concentrations range between 4 and 12%.

Various changes may be made in the details of the invention, as disclosed, without sacrificing the advantages thereof, nor departing from the scope of the appended claims. Furthermore, although the present invention has been disclosed and discussed with particular regard to its exceptional advantages, in terms of an elbow prosthesis, it may be understood that the invention may be employed in several surgical applications wherein such a prosthesis is desired.

What is claimed is:

1. An elbow prosthesis comprising:
   (a) an intermediate insert having an inner bore and first and second outer surfaces perpendicular to an axis of the inner bore, the insert being a single insert comprising first and second U-shaped parallel members, each of said U-shaped members having a right leg and a left leg with a slot therebetween and connected by a bottom portion, said U-shaped parallel members being arranged so that the slots form the inner bore, the left legs of said first and second U-shaped members being connected by an integral portion and the right legs of said U-shaped members having an opening therebetween;
   (b) a humeral member including means for engaging the intermediate insert by engaging the first and second outer surfaces; and
   (c) an ulnar member including means for engaging the inner bore, the axis of said inner bore forming a pivot point between the humeral member and the ulnar member.

2. The elbow prosthesis of claim 1 wherein said ulnar member is comprised of a curved surface and a support projecting from the curved surface and terminating in a cylindrical member separate from and concentric with the curved surface.

3. The elbow prosthesis of claim 2 wherein the curved surface has a radius of curvature with a center axis of the curved surface coinciding with the axis of the inner bore.

4. The elbow prosthesis of claim 1 wherein said intermediate insert further comprises raised surfaces formed on an inner periphery of the corresponding legs of said first and second U-shaped members for enclosing said means for engaging the inner bore.

5. The elbow prosthesis of claim 4 wherein said humeral member further includes platform means for engaging and stabilizing said protrusions of said intermediate insert.

6. The elbow prosthesis of claim 5 wherein the platform means of said humeral member further comprises a cavity formed therein for engaging said integral portion connecting said right legs of said first and second U-shaped members.

7. The elbow prosthesis of claim 1 further including means for engaging a radius and a radial member having a concave surface for engaging said means for engaging a radius, the concave surface being made of a plastic material suitable for surgical implantation in the human body, the humeral member and the ulnar member being made of a metal suitable for implantation in the human body and the intermediate insert being made of a plastic material suitable for surgical implantation in the human body.

8. The elbow prosthesis of claim 7 wherein the radial member is made of a plastic material suitable for surgical implantation in the human body and having an X-ray wire located therein.

9. The elbow prosthesis of claim 7 wherein the radial member has a concentration of barium sulfate of between 4 and 12% by weight.

10. An elbow prosthesis comprising:
    (a) an intermediate insert having an inner bore and first and second outer surfaces perpendicular to an axis of the inner bore;
    (b) a humeral member comprising a forkshaped portion having first and second flat fork branches formed in substantially parallel planes, the opposing surfaces of said flat fork branches each including an L-shaped platform for engaging the first and second outer surfaces of the intermediate insert and means for engaging a natural or artificial radius including a spherical portion therein; and
    (c) an ulnar member including means for engaging the inner bore, the axis of said inner bore forming a pivot point between the humeral member and the ulnar member.

11. An elbow prosthesis comprising:
    (a) an intermediate insert having an inner bore and first and second outer surfaces perpendicular to an axis of the inner bore, the insert being single insert comprising first and second U-shaped parallel members, each of said U-shaped members having a right leg and a left leg with a slot therebetween and connected by a bottom portion, said U-shaped parallel members being arranged so that the slots form the inner bore, the left legs of said first and second U-shaped members being connected by an integral portion and the right legs of said U-shaped members having an opening therebetween;
    (b) a humeral member comprising a fork-shaped portion having first and second flat fork branches formed in substantially parallel planes, the opposing surfaces of said flat fork branches each including an L-shaped platform for engaging the first and second outer surfaces of the intermediate insert and means for engaging a natural or artificial radius including a spherical portion therein; and
    (c) an ulnar member including means for engaging the inner bore, the axis of said inner bore forming a pivot point between the humeral member and the ulnar member.

* * * * *